United States Patent [19]

Gansow et al.

[11] Patent Number: 4,472,509

[45] Date of Patent: Sep. 18, 1984

[54] METAL CHELATE CONJUGATED MONOCLONAL ANTIBODIES

[76] Inventors: Otto A. Gansow, 3003 Van Ness, NW., W 524, Washington, D.C. 20008; Mette Strand, 807 Harper House, Village of Cross Keys, Baltimore, Md. 21210

[21] Appl. No.: 386,110

[22] Filed: Jun. 7, 1982

[51] Int. Cl.$^3$ .................... A61K 39/00; A61K 39/42; A61K 43/00; A61K 49/00
[52] U.S. Cl. .................... 436/548; 436/804; 436/819; 436/813; 436/811; 260/429 J; 424/1.1; 424/9; 424/85; 424/86
[58] Field of Search .................... 424/1, 1.1, 1.5, 85, 424/86; 436/547, 548, 73, 76, 82, 84, 543–546, 804, 819, 813, 811; 560/117; 549/385; 260/429 J

[56] References Cited

U.S. PATENT DOCUMENTS

| | | | |
|---|---|---|---|
| 3,961,038 | 6/1976 | Benes | 424/1 |
| 4,196,265 | 4/1980 | Koprowski et al. | |
| 4,311,688 | 1/1982 | Burchiel et al. | 424/1 |
| 4,323,546 | 4/1982 | Crockford et al. | 424/1 |
| 4,331,647 | 5/1982 | Goldenberg | |
| 4,339,426 | 7/1982 | Meares et al. | 424/1 |
| 4,348,376 | 9/1982 | Goldenberg | |
| 4,349,689 | 9/1982 | Aristoff | 560/117 |
| 4,352,751 | 10/1982 | Wieder et al. | 260/112 R |
| 4,361,544 | 11/1982 | Goldenberg | 424/1 |
| 4,364,920 | 12/1982 | Winchell | 424/1 |
| 4,385,046 | 5/1983 | Milbrath et al. | 424/9 |
| 4,401,824 | 8/1983 | Aristoff | 549/385 |

FOREIGN PATENT DOCUMENTS

| | | |
|---|---|---|
| 0038546 | 10/1981 | European Pat. Off. |
| 0066786 | 12/1982 | European Pat. Off. |

OTHER PUBLICATIONS

Scheinberg et al., Science, vol. 215, pp. 1511–1513, (3-82).
Krejcarek, G. E. et al., Biochemical Biophysical Research Communications, vol. 77(2), pp. 581–585, 1977.
Khaw et al., Science, vol. 209, pp. 295–297, (1980).
Meares et al., Proc. Natl. Acad. Sci. U.S.A., 73: 3803–3806, (1976).
Hnatowich et al., Int'l. J. App. Radiat. Isot., 33: 326–332, (1982).
Paik et al., J. Nuc. Med., 22: 32, (1981).
Paik et al., J. Radioanal. Chem., 57: 553–564, (1980).
Bloomer et al., Science, 212: 340–341, (1981).
Zucchini et al., Int. J. Nucl. Med. & Biol., 9: 83–84, (1982).
Scheinberg et al., "Leukemic Cell Targeting and Therapy by Monoclonal Antibody in a Mouse Model System," (1982), Cancer Research 42:44–49.
Scheinberg et al., "Targeting in Erythroleukemic Mice: Radioiodinated and Chelated Radiometal-Conjugated Monoclonal Antibody," in Monoclonal Antibodies in Drug Development, pp. 159–171, (J. T. August ed. 1982).

Primary Examiner—Brooks H. Hunt
Assistant Examiner—M. Moskowitz
Attorney, Agent, or Firm—Banner, Birch, McKie & Beckett

[57] ABSTRACT

Methods of manufacturing and purifying metal chelate conjugated monoclonal antibodies are described. The chelated metal may be one which emits alpha, beta or gamma radiation, or positrons. Alternatively, the metal can be one which is fluorogenic or paramagnetic. The conjugates are suited for diagnostic and therapeutic uses.

29 Claims, No Drawings

METAL CHELATE CONJUGATED MONOCLONAL ANTIBODIES

This invention was made under a grant or award from the Department of Health and Human Services.

TECHNICAL FIELD

This invention relates to metal chelate conjugated monoclonal antibodies.

BACKGROUND OF THE INVENTION

The development of monoclonal antibodies has made possible new diagnostic and therapeutic techniques. Monoclonal antibodies are highly specific and can be used, for example, as vehicles to deliver other substances to specific target sites in vivo. It has been suggested in the literature that diethylenetriaminepentaacetic acid (DTPA) can form stable metal complexes when attached to protein. Krejcarek et al., 77 Biochem. & Biophys. Res. Commun. 581 (1977). Imaging of target sites iv vivo with radiometal-DTPA conjugated polyclonal antibodies prepared according to the method of Krejcarek have also been reported. Khaw et al., 209 Science 295 (1980). Despite separation by gel chromatography and dialysis of free and chelated metal from the metal chelate conjugated polyclonal antibodies targeted for a myocardial infarct, the gamma camera images show that a high proportion of the radiometal localized in the liver.

There remains an obvious need for an effective method to prepare metal conjugated monoclonal antibodies which permit highly selective delivery of metals to predetermined sites in vivo.

SUMMARY OF THE INVENTION

It is an object of this invention to provide an aqueous solution of metal chelate conjugated monoclonal antibodies in which substantially all of said metal is stably complexed by the chelate portion of the conjugate.

It is another object of the present invention to provide a method for preparing metal chelate conjugated monoclonal antibodies that retains their inherent biological activity and specificity substantially unimpaired.

It is still another object of the present invention is to provide a method for preparing metal chelate conjugated monoclonal antibodies substantially free of adventitously bound and weakly chelated metal.

It is a further object of the present invention to provide a rapid purification method for preparing metal chelate conjugated monoclonal antibodies.

It is a still further object of the present invention to provide an improved method of preparing metal chelate conjugated monoclonal antibodies in which the chelate is derived from diethylenetriaminepentaacetic acid.

These and other objects of the present invention are accomplished by one or more of the embodiments of the present invention.

One embodiment of this invention is directed to an aqueous solution of metal chelate conjugated monoclonal antibodies in which substantially all of said metal is stably complexed by the chelate portion of the conjugate.

In another embodiment, the present invention contemplates a method for preparing metal chelate conjugated antibodies comprising adding a metal salt to an aqueous solution of chelate conjugated monoclonal antibodies and a buffer, said solution being maintained at a pH within the range of about 3.2 to about 9 throughout chelation without the addition of a strong acid or strong base.

The present invention also contemplates a method for preparing nonferrous metal chelate conjugated antibodies substantially free of chelated iron comprising contacting a nonferrous metal salt and an aqueous solution of chelate conjugated monoclonal antibodies at a pH within the range of from about 3.2 to about 9 in the presence of a water soluble, non-chelatable, biologically innocuous reducing agent.

In yet another embodiment, the present invention contemplates a method of purifying metal chelate conjugated monoclonal antibodies comprising passing an aqueous solution containing metal chelate conjugated monoclonal antibodies through a chromatography column, said column having one or more layers selected from the group consisting of an ion retardation resin, an anion exchange resin, a cation exchange resin and a chelating ion exchange resin, and a final layer comprising a sizing matrix.

A further embodiment of the present invention contemplates a method of preparing chelate conjugated monoclonal antibodies comprising contacting a carboxycarbonic anhydride of diethylenetriaminepentaacetic acid in an organic solvent with an aqueous solution of monoclonal antibodies at a pH maintained in a range of from about 6 to about 7.2 to produce chelate conjugated monoclonal antibodies; and recovering said chelate conjugated monoclonal antibodies having their biological activity and specificity substantially retained.

This invention provides metal chelated conjugated antibodies which retain their biological activity and specificity, and which are substantially free of adventitiously bonded metals. Adventitiously bonded metals are not stable and result in free metal entering the blood. Metals which are released in the blood can be bound by transferrin or other metal binding proteins (e.g., ferritin) which are present in blood. Such bound metals are retained in the circulatory system for considerable periods of time and are cleared by the reticuloendothelial system (RES). Such clearance results in a concentration of the metal in the liver and spleen. It is apparent that random, long term circulation of radioactive metals in the body or concentration of radioactive metals in the liver and spleen are highly undesirable. The practice of this invention can alleviate these serious problems.

In one of its aspects, the present invention avoids the use of strong acids or bases which can have a deleterious effect on the biological activity of the antibody. The metal chelate conjugated antibodies are purified in accordance with another aspect of this invention without the use of lengthy dialysis. Lengthy dialysis is undesirable for any radioactive material and is particularly disadvantageous when radioactive metals with short half lives are employed for diagnostic or therapeutic purposes. The longer the purification procedure, the lower the effective dose which can be delivered to the target site.

DETAILED DESCRIPTION OF THE INVENTION

Monoclonal antibodies are immunoglobulins of well-defined chemical structure, in contrast to polyclonal antibodies which are heterogeneous mixtures of immunoglobulins. A characteristic feature of monoclonal antibodies is reproducibility of function and specificity, and such antibodies can be and have been developed for a wide variety of target antigens, including tumor cells.

Methods for obtaining monoclonal antibodies have been extensively discussed and are well-known in the art. A useful text is Monoclonal Antibodies (R. H. Kennett, T. J. McKearn & K. B. Bechtol eds. 1980). See also Koprowski et al. U.S. Pat. No. 4,196,265. The selection of a monoclonal antibody for the practice of this invention will depend upon the end use for which the metal chelate conjugated monoclonal antibody will be employed. Such selection is within the skill of the art.

The antibodies are generally maintained in an aqueous solution that contains an ionic compound. A physiologic normal saline solution is very often employed and is widely available. Other ionic solutions, such as those containing sodium or potassium phosphate, sodium carbonate and the like, are known in the art and may also be employed.

A wide variety of organic chelating agents or ligands can be conjugated to monoclonal antibodies. Organic ligands to be conjugated to monoclonal antibodies may be chosen from among either the natural or synthetic amines, porphyrins, aminocarboxylic acids, iminocarboxylic acids, ethers, thiols, phenols, glycols and alcohols or the polyamines, polyaminocarboxylic acids, polyiminocarboxylic acids, aminopolycarboxylic acids, iminopolycarboxylic acids, nitrilocarboxylic acids, dinitrilopolycarboxylic acid, polynitrilopolycarboxylic acids, ethylenediaminetetracetates, diethylenetriaminepenta or tetracetates, polyethers, polythiols, cryptands, polyetherphenolates, polyetherthiols, ethers of thioglycols or alcohols, polyaminephenols, all either acyclic, macrocyclic, cyclic, macrobicylclic or polycyclic, or other similar ligands which produce highly stable metal chelates or cryptates. Obviously, the choice of the ligand depends upon the metal to be chelated and is within the skill of the art.

The ligand used in certain embodiments of this invention possesses a nonmetal bonded organic functional group suitable for bonding to the monoclonal antibody. Functional groups may be chosen from among the carboxylic acid groups, diazotiazable amine groups, succinimide esters, anhydrides, mixed anhydrides, benzimidates, nitrenes, isothiocyanates, azides, sulfonamides, bromoacetamides, iodoacetamides, carbodiimides, sulfonylchlorides, hydrazides, thioglycols, or any reactive functional group known in the art as a biomolecular conjugating or coupling agent.

Many aspects of the present invention employ a derivative of diethylenetriaminepentaacetic acid (DTPA). It has been found that DTPA ligands tightly bind metal ions and that the DTPA derivative (hereinafter referred to as chelate) forms a chelate conjugated monoclonal antibody that is highly stable, both with respect to the metal chelate binding and with respect to chelate-antibody conjugate. These properties are of great importance, particularly for in vivo applications. For example, if the chelate releases the metal ion after introduction into the blood, these ions will tend to be bound by transferrin, or the like, and be distributed generally in the circulatory system of the body. Moreover, the ions will ultimately tend to collect and remain in organs such as the liver and spleen. These effects can have serious consequences depending on the toxicity of the metal and its radioactivity. Furthermore, if the chelate does not form a highly stable conjugate with the antibody, there is a significant reduction in the amount of metal delivered to the target site and a corresponding decrease in efficacy. If the conjugate is used for diagnostic purposes release of the metal can undesirably increase background radiation.

In the preparation of the metal chelate conjugated monoclonal antibodies of the present invention, it is important to avoid metal contamination from outside sources. Labware should be plastic or glass cleansed of exogenous metal. All stock solutions should be metal depleted by, for example, column chromotography with a suitable resin.

The preferred chelate is prepared from an amine salt of DTPA. Amine is used broadly and includes primary, secondary and tertiary amines that will completely deprotonate the DTPA. Selection of an appropriate amine is within the skill of the art and the efficacy of any amine (including ammonia) can readily be determined. A particularly preferred amine is triethylamine. At least about 5 equivalents of the amine is added to an aqueous solution of DTPA and warmed to complete the reaction. The reaction produces a pentakis(amine)DTPA salt according to the following equation wherein triethylamine is the amine:

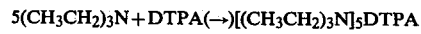

$$5(CH_3CH_2)_3N + DTPA (\rightarrow)[(CH_3CH_2)_3N]_5DTPA$$

Solid DTPA-amine salt can be recovered by evaporating or freeze-drying the solution to remove the water and excess amine.

The actual chelate is a DTPA derivative. A functional group is added to the DTPA and the DTPA is bonded through it to amine groups on the monoclonal antibody. Esters of a haloformic acid are reacted with the DTPA-amine salt to make the chelate employed by the present invention. By ester of a haloformic acid is meant an ester of the general formula $XC(O)-O-R$ wherein X is a halogen, preferably a chloride, and R is any suitable functional group, preferably containing not more than about 6 carbon atoms. The selection of R and X is within the skill of the art taking into consideration the stability of the chelate and steric hinderance when the chelate is reacted with the monoclonal antibody. A preferred ester is isobutylchloroformate.

In an exemplary preparation, approximately equimolar amounts of haloformic acid ester and DTPA-amine salt are dissolved in a polar organic solvent such as pure, dry acetonitrile. Excess of the halomformic acid ester should be avoided because it will block a metal chelation site on the modified DTPA ligand. The temperature of the reaction is generally not critical and can be chosen to provide a salt that is either partially or substantially precipitated. The reaction preferrably is carried out at a temperature low enough to precipitate substantially all of the haloamine salt by-product of the reaction. When the amine employed is triethylamine and the ester is an ester of chloroformic acid, the temperature should be in the range of from about $-20°$ C. to about $-70°$ C. Maintaining the temperature in this range drives the equilibrium reaction to the right, producing a high yield of a mixed carboxycarbonic anhydride of DPTA according to the following equation:

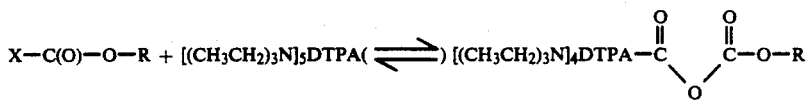

By carrying out the above reaction in the temperature range specified, a high concentration of the chelate can be produced substantially free of the haloamine salt by-product. For example, approximately 0.25 mM of the pentakis(triethylamine)DTPA salt can be dissolved in 0.5 ml acetonitrile and reacted with 35 microliters of isobutylchloroformate. After approximately 45 minutes at −70° C., the solution can be centrifuged to remove the precipitate leaving a supernatant liquid containing the desired chelate at a concentration of about 0.5M. The chelate is desirably introduced into the chelate-antibody conjugation reaction at a concentration of at least about 0.25M in the organic solvent. Such concentrations of chelate permit the use of relatively small amounts of organic solvents in the conjugation reaction mixture. Excessive amounts of organic solvent in the reaction mixture should be avoided because the solvent can produce adverse effects with respect to the biological activity and specificity of the antibody.

The chelate conjugated monoclonal antibody is formed by adding the chelate in the organic solvent to an aqueous saline antibody solution. It is important to carry out the reaction of the modified DTPA and antibody at a pH not higher than about 7.2. The chelate-antibody reaction competes with the decomposition of the chelate caused by its reaction with water. If the pH is too low, however, the chelate undergoes acid catalysed decomposition and the biological activity and specificity of the antibody is diminished. The pH is desirably in the range of from about 6.0 to about 7.2, preferably as close to 7.0 as practicable. In this range, the reaction of the DTPA chelate with water is less detrimental to the chelate-antibody reaction.

While the above discussion has focused on DTPA, it is within the skill of the art to form conjugates employing other ligands. See, e.g., 73 Proc. Natl. Acad. Sci. U.S.A. 3803 (Nov. 1976).

To preserve the maximum biological activity of the antibody, the use of strong acids or bases to adjust pH should be avoided for any chelate-antibody preparation. Use of a strong acid or base can cause localized denaturation in the solution. The pH can be controlled in the aqueous solution of monoclonal antibody by including a suitable buffer. For example, $NaHCO_3$ at a concentration of approximately 0.1M can be used. Other buffers such as MES (2-(N-morpholino)ethane sulfonic acid) are known in the art and may also be employed. The choice of an appropriate buffer is within the skill of the art.

When the chelate solution is added to the aqueous antibody solution, both should be at about 0° C. The temperature of the solution generally should not be allowed to rise above about 4° C. during the course of the reaction. Use of temperatures in the range of about 0° to about 4° C. tends to avoid decomposing the antibody and also reduce chelate decomposition. Duration of the reaction is not critical so long as the reaction is permitted to go to completion and the solution may be left in the cold overnight.

The chelate-to-antibody mole ratio may vary widely depending upon the use for which the conjugate is intended. The mole ratio of chelate-to-antibody can broadly range from about 0.1 to about 10 or higher and preferably from about 0.25 to about 5. In many instances the mole ratio of chelate to antibody will range from about 0.5 to about 3.

In general an excess of chelate is employed in the reaction because the chelate will decompose to some extent in the aqueous solution. The number of chelates bound per molecule of antibody will be a function of both the concentration of the chelate and the concentration of the antibody in the reaction mixture, with high concentrations tending to provide more chelates per antibody. If the amount of antibody employed is relatively small and a relatively dilute solution is employed, a substantial excess of chelate may be required. For example, a molar excess of approximately 600:1 of chelate may be required to react with an antibody solution having a protein concentration of about 5 to 10 mg per ml in order to provide approximately 1.5 chelates bonded per molecule of antibody. Molar excesses as low as 100:1 can be employed, however, and still produce an average of about 0.5 chelates bond per molecule of antibody. Adding too many chelate molecules per antibody molecule can reduce the biological activity and specificity of the antibody.

When the addition of the chelate to the antibody has gone to completion, substantial amounts of decomposed chelate may be present in the solution. This can occur for any chelate-antibody conjugate. The decomposed chelate should be removed while retaining the biological activity and specificity of the antibody. Dialysis or chromatography can, for example, be employed. If desired, a first dialysis against dilute ascorbic acid and EDTA solution to remove any residual iron which may be present in the chelate or the protein. A purified chelate conjugated antibody can be produced by dialysis of the reaction mixture over a 48 hour period against three 1 liter changes of an aqueous solution at about 4° C. and a pH of about 6 containing 50 mM citrate and 200 mM sodium chloride with 1 ml Chelex 100 resin (Bio-Rad) in the dialysis vessel. A final dialysis into 1 liter of solution containing 10 mM MES and 200 mM sodium chloride at 4° C. and pH 6 completes purification of the protein. Variations of dialysis procedures are known and are within the skill of the art.

The metals which may be employed in the present invention may include radioactive or nonradioactive elements with a valence of three or higher. Monovalent or divalent metals generally do not form sufficiently stable chelates for the purposes of this invention. Representative radioactive elements may include d-block transition metals, the group IIIA, IVA, VA metals, the lanthanides or the actinides. Nonradioactive metals may be selected, for exammple, for their useful physical properties such as paramagnetism, fluorescence, or phosphorescence. Representative nonradioactive metals include most lanthanides and some first row, d-block elements. While this invention is discussed in terms of metals or metal chelates, it will be understood that metal ions are, in fact, chelated in the conjugate.

If the metal chelate conjugated monoclonal antibody is to be used for imaging in vivo, a gamma or positron emitting radiometal, such as indium-111 (gamma) or gallium-68 (positron), can be used, depending upon the chosen method of detection. For purposes of therapy, the radiometal can be alpha (e.g., bismuth-212), beta (e.g, scandium-47) or Auger electron emitter. An alpha emitter, such as bismuth-212 is desirably employed for therapy. Paramagnetism, fluorescence and phosphorescence can be used, for example, for in vitro tests. The choice of any particular metal and valence state is within the skill of the art.

Metal chelation is carried out in an aqueous solution and, once again, desirably avoids the use of strong acids or bases. Metal chelation for any chelate-antibody conjugate is carried out at a pH which does not significantly reduce the biological activity or specificity of the antibody. Generally, the acceptable range is from about pH 3.2 to about pH 9, however, particular antibodies may have to be restricted to a narrower range. At a pH below about 3.5, adventitious binding of metal ions to antibodies is substantially impaired for many metals. A preferred range, therefore, is often from about pH 3.2 to about pH 3.5. Factors peculiar to solutions of the metal employed, however, may permit a pH above 3.5. The selection of the appropriate pH within the range is within the skill of the art.

In the present invention, a weakly chelating acid or base is desirably employed as a buffer. Citric acid or glycine are useful buffers. Still other buffers are, of course, known in the art. The present invention contemplates a solution of chelate conjugated antibodies adjusted to the desired pH with a weakly chelating acid or base buffer and without the addition of a strong acid or base. To this solution is added a metal salt. If the metal salt is in solution, that solution also has its pH adjusted with a chelating buffer. The pH of the metal solution, however, can be adjusted with strong acids or bases prior to its addition to the chelate conjugated antibody solution.

Any acceptable metal salt can be employed to make the metal chelate conjugated monoclonal antibodies. Typical salts may include halides (e.g, chlorides), nitrates, perchlorates, or the like. The metal salt is employed in as high a concentration as is practicable. When the metal is radioactive, radiation exposure of those preparing or handling the metal chelate conjugated monoclonal antibodies will probably set a limit below one equivalent of metal per chelate binding site. In these instances, the method of the present invention is particularly useful because efficient production of the metal chelate conjugated monoclonal antibodies can be achieved. If the metal is not radioactive, a substantial excess is desirable.

When it is desired to incorporate technetium-99m into chelate conjugated monoclonal antibodies it will usually be necessary to reduce the technecium to the +3 or +4 valence state because it is normally commercially available as the pertechnetate. The preparation should also be carried out in the absence of oxygen, for example, in a glove box under a nitrogen atmosphere. An example of a suitable reducing agent is sodium dithionite.

The duration of the reaction is not critical unless the pH is near the outside limits of pH acceptable to the antibody. At or near such pH limits, the reaction times generally should be under about 1 hour and preferably about 30 minutes or less. Indeed, from the standpoint of economy of time, reaction times generally within these periods are desired. The reaction is usually completed by adding trisodium citrate in sufficient quantity so that the solution pH is raised to a point that the metal conjugate is no longer labile. It has been determined that most DTPA complexes are at especially stable at a pH of about 6. Other weak bases, or acids when the reaction is above pH 6, may be used so long as they do not adversely affect the antibodies. Their selection is within the skill of the art.

The reaction solution will generally require purification prior to its use in vivo, and may also require purification prior to in vitro use. Nonbonded metal and adventitiously bonded metal should be removed. The discussion herein refers to adventitiously bound metal ions. Some of the metal, however, may be insecurely held by the chelates and acts in the same manner as adventitiously bound metal ions.

When a radioactive metal is employed which has a short half life, it is especially important that the purification step be as expeditious as possible. The present invention contemplates a relatively fast purification by use of chromatography and this facet of the invention is applicable to chelate-antibody conjugates in general. By employing one or more ion exchange, retardation or chelating resins in conjunction with a sizing matrix (e.g., gel) the metal chelate conjugated monoclonal antibodies of the present invention can be quickly and thoroughly purified.

Different ion exchange resins can be employed singly, or any combination of an ion retardation resin, a cation exchange resin, an anion exchange resin or a chelating ion exchange resin can be employed. The selection of an appropriate resin or resins, their extent of class-linkage, chemical form and mesh size is within the skill of the art.

Cation exchange resins employed in the present invention frequently are strongly acidic polystyrene gel-type resins (e.g., Dowex 50W $\times$ 8) or other non-polystyrene strongly acidic resins such as Zeocarb 215 (Permutit Co.). Additional suitable acidic resins can include weakly acidic gel polystyrene resins, macroporous gel polystyrene resins, or macroreticular carboxylic acid cation exchange resins. Anion exchange resins can include strongly basic polystyrene gel-type resins (e.g., Dowex 1$\times$8) or other less basic resins such as pyridinium polymer-type and phenolic polyamine-type resins. Chelating resins may be Chelex 100, or any resin of the type which is a styrene divinyl benzene copolymer containing paired imminodiacetate ions (e.g, Dowex A-1). Useful retardation resins include those containing paired anion and cation exchange sites (e.g., Bio-Rad AG 11-A8). These resins are usually made by polymerizing acrylic acid inside a strongly basic resin such as one having quaternary ammonium groups in a styrene-divinyl benzene copolymer lattice. The above discussion includes only representative examples of each resin; still other resins are also known in the art. A compendium of commercially available resins with brief descriptions of their properties and applications is contained, inter alia, in Bio-Rad Laboratories, 1982 Price List H. The choice and combination of resins will depend upon the particular separation problem encountered and is within the skill of the art in view of the disclosure herein. A useful reference is J. Khym, Analytical Ion-Exchange Procedures in Chemistry and Biology (1974).

Sizing matrices are also well known in the art. These include polyacrilamides, agraroses, polysaccharides or the like. A particularly useful sizing matrix is a polysaccharide gel (e.g., Sephadex G-50 gel). Examples of polyacrilamide gels are the Bio-Gel P Series (Bio-Rad Labs). The choice of the sizing matrix will depend upon the protein to be purified and is within the skill of the art.

In the practice of this invention the various resins can be established as layers within a column and the solution to be purified can be fed either downwardly through the column or upwardly through the column. Downward feed is a preferred laboratory technique when radioactive compounds are employed because gravity flow requires little or no auxiliary equipment or instrumentation. The choice of bed heights, flow rates, and the like are easily within the skill of the art.

It appears that highly charged metals are adventitiously bound, at times, by the antibody at ionic sites along the surface of the protein. At other times adventitiously bound metals appear to be included with the folds of the antibody protein. These metals can be released into solution but also can be reabsorbed from the solution in an equilibrium-type process. The retardation or ion exchange resins employed in the purification of this invention are used in order to shift the equilibrium and permit metals to be removed from the antibody. For example, as the antibody passes through an ion retardation resin, the passage of metal ions in the solution is slowed, but the protein is not. Adventitiously bonded, higly charged (+3 or higher), metal ions are then released into the solution to reestablish equilibrium. As those ions are released into solution, however, they in turn are retarded by the resin to cause a continuing metal ion release by the antibody.

A level of ion exchange resin may be employed below the ion retardation resin to tightly bind the separated, highly charged ions and to continue the separation process. As the resin depletes the protein solution of free, highly charged ions, equilibrium is again reestablished between free and adventitious metal ions. However, throughout this process, metal ions inside the chelate are retained with the antibody.

It has been determined, however, that mere use of an ion retardation or ion exchange resin is not satisfactory to provide an effective removal of substantially all adventitiously bound metals. In order to complete the purification a sizing matrix is employed. The antibody solution which enters the matrix is areadly partially depleted in free, highly charged metal ion content. In the sizing matrix, further depletion occurs. As the solution moves through the matrix, the antibodies are not retarded while the ions are. The resulting solution taken off from the sizing matrix is substantially free of adventitiously bound metals. Such loosely bound metals can be reduced to not more than about six percent of the total metal content of conjugate so that at least about 94% of the metal carried by the conjugate is bound by the chelate stably. Desirably, at least about 97% of the total metals bound by the chelate. It is possible to obtain metal levels in which 98% or more of the metal is bound by the chelate. Dialysis can be employed to determine stably bound metal content.

A preferred method of purification for metals such as indium is an ion retardation resin (Bio-Rad AG 11-A8) over a cation exchange resin (Bio-Rad AG 50WX8) and a gel (Pharmacia Sephadex G-50). In the purification of technicium chelate conjugated monoclonal antibodies for the present invention, the preferred column contains an ion retardation resin (Bio-Rad AG 11-A8) over a cation exchange resin (Bio-Rad 50WX8) over an anion exchange resin (Bio-Rad AG 1X8) and a sizing matrix gel (Pharmacia Sephadex G-50).

In the process of this invention, the antibody is retained in nonaggregated form. Aggregation of antibodies, whether by clumping or by cross-linking, results in a loss of antibody specificty which, of course, is undesirable. Aggregation can be caused by excessively high concentrations of antibodies in a carrier, or by contact with chemicals that cause protein cross-linking such as, for example, carbodiimdes. Standard sedimentation tests, size matrixing, or the like, can be employed to determine if the antibodies have aggregated. Indeed, the antibody specificity tests discussed herein will reflect aggregation as a loss of specificity.

The activity and specificity of the conjugated antibody products of this invention are maintained at a level of at least about 80%, and preferably at least about 90% of the activity and specificity of the antibody that was employed to produce the conjugate. Particularly preferred solutions are characterized by antibody activity and specificity of at least about 95% and, indeed, products have been produced which retain the activity and specificity of the original antibody virtually unchanged. The activity and specificity of antibodies are routinely measured in the art by binding of antibodies, in vitro, to an epitope. The degree of activity and specificity of the final antibody product can readily be determined simply by repeating the initial test with the final conjugated product.

The metal chelate conjugated antibodies of this invention can be administered in vivo in any suitable pharmaceutical carrier. As noted earlier, a physiologic normal saline solution can appropriately be employed. Often the carrier will include a minor amount of carrier protein such as human serum albumin to stabilize the antibody. The concentration of metal chelate conjugated antibodies within the solution will be a matter of choice. Levels of 0.5 mg per ml are readily attainable but the concentrations may vary considerably depending upon the specifics of any given application. Appropriate concentrations of biologically active materials in a carrier are routinely determined in the art.

The effective dose of radiation or metal content to be utilized for any application will also depent upon the particulars of that application. In treating tumors, for example, the dose will depnd, inter alia, upon tumor burden, accessability and the like. Somewhat similarly, the use of metal chelate conjugated antibodies for diagnostic purposes will depend, inter alia, upon the sensing apparatus employed, the location of the site to be examined and the like. In the event that the patient has circulating antigen in addition to those located at the site, the circulating antigens can be removed prior to treatment. Such removal of antigens can be accomplished, for example, by the use of unlabeled antibodies, or by plasmaphoresis in which the patient's serum is treated to remove antigens.

The following examples are included to better illustrate the practice of this invention. These examples are included for illustrative purposes only and are not intended in any way to limit the scope of the invention.

EXAMPLE I

One hundred miligrams of DTPA was weighed into a flask and to this was added 1 ml of water. This solution was reacted with 0.125 g redistilled triethylamine. The reaction solution was warmed to complete the reaction and a solid product was collected by freeze drying.

The freeze dried solid was dissolved in 0.5 ml of pure, dry acetonitrile and 35 ul isobutylchloroformate added at a temperature of approximately −20° C. and brought down to about −70° C. After about 45 minutes, the solution was centrifuged in an Eppendorf vial. The supernatant liquid was collected which contained the desired mixed carboxycarbonic anhydride of DTPA at a concentration of approximately 0.5M.

The monoclonal antibody employed was designated 103A5 and was obtained by fusing P3X63Ag8 mouse myeloma cells with the isolated spleen cells of C56B1/6 mice which had been immunized with purified retrovirus glycoprotein of 70,000 daltons (gp70) obtained as described by M. Strand and J. T. August, 251 J. Biol. Chem. 559 (1976). The fusion was carried out as described by M. Strand, 77 Proc. Natl. Acad. Sci. U.S.A. 3234 (1980).

A 114 ul solution containing 2 mg of monoclonal antibody 103A5 in 0.1M $NaHCO_3$ at a pH of approximately 7.2 and 150 mM sodium chloride was prepared and pipetted into a Nunc vial. Then, 33 ul of a 0.1M $NaHCO_3$ solution at a pH of 7.0 was added to the vial. Finally, 26.4 ul of the mixed carboxycarbonic anhydride of DTPA (0.5M in acetonitrile) was added after cooling the chelate and antibody solutions to approximately 0° C. The reaction was allowed to proceed overnight.

The product was first dialyzed at 4° C., against one liter of 30 mM ascorbic acid, 5 mM EDTA, 200 mM NaCl and 20 mM of sodium citrate (pH 7.0). The resulting solution was dialyzed at 4° C. against three one liter changes of 50 mM citrate, 200 mM sodium chloride at pH 6.0, and 1 ml Chelex 100 resin (Bio-Rad) over a 48 hour period. Finally, the resulting solution was dialyzed for 8 hours against one liter of a solution that had a concentration of 10 mM MES and 200 mM sodium chloride at pH 6.0. Approximately 1.7 mg of chelate conjugated monoclonal antibody was recovered. Analogous experiments employing C-14 labled DTPA were analyzed by scintillation counting and shown to contain approximately 1.5 chelates per antibody molecule.

Forty microliters of Indium-111 chloride solution (New England Nuclear Corp.) was adjusted to pH 3.0 by the addition of 11.4 ul of 0.4M citric acid at pH 5.0. A separate solution was prepared containing 250 micrograms of chelate conjugated monoclonal antibody in a total volume of 21.6 microliters. The solution had a concentration of 200 mM sodium chloride and 10 mM MES at a pH of 6.0. The solution was adjusted to pH 4.6 by the addition of 6 ul of 0.25M citric acid at a pH of 3.0.

The metal chelate conjugated monoclonal antibody was prepared by combining the indium chloride and chelate conjugated antibody solutions and allowing them to react for approximately 30 minutes at ambient temperature. The reaction was terminated by adding 25 ul of a saturated solution of trisodium citrate to adjust the pH to about 6.

The chelate conjugated antibody was purified by chromatography on 9 cm long column containing 1.0 ml of an ion retardation resin (AG 11-A8 available from Bio-Rad) above 1.0 ml of a cation exchange resin (AG-50-WX8, H+ form, 200-400 mesh available from Bio-Rad) above 7 ml of Sephadex G-50 gel (Pharmacia). A solution with concentrations of 200 mM sodium chloride and 10 mM MES at a pH of 6.0 was used as the eluant and was used pre-equilibrate the column.

The eluate was collected in 0.5 ml fractions. The two fractions with most of the protein were shown to contain 150 ug of monoclonal antibody labeled with 157.1 microcuries Indium-111. Dialysis at 4° C. against one liter of an aqueous solution of 20 mM MES and 200 mM sodium chloride at pH 6.0 showed less than 6% loss of Indium. The antibody was shown to retain substantially 100% of its biological activity and specificity by in vitro tests. In vivo imaging in leukemic mice highlighted the tumor site in the spleen. When administered to normal mice there was no uptake by the spleen.

EXAMPLE II

A hybridoma was obtained by fusing P3 653 mouse myeloma cells with the isolated spleen cells of C56B1/6 mice which had been immunized with purified tumor-associated ferritin isolated from the human spleen. A hybridoma was isolated that produced an anti-ferritin antibody designated 263D5. The antibody was specific for human ferritin and did not react with ferritin of other mammalian species.

The procedure of Example 2 was repeated to provide an indium-111 containing DTPA conjugated monoclonal antibody. A physiologic normal saline solution containing the metal chelate conjugated monoclonal antibody was injected into normal and leukemic mice. In both the leukemic and normal mice, radio imaging showed that there was no concentration of radio labeled metal. These tests demonstrated that the chelate was stable in vivo both with respect to the chelate-antibody conjugation and with respect to the retention of the radioactive metal. Neither the spleen nor the liver was highlighted in the images.

EXAMPLE III

Indium-111 chelate conjugated monoclonal antibodies were prepared from an antibody specific for human breast tumor. The hybridoma that produced the antibody was prepared from a fusion of mouse myeloma and mouse spleen cells. The hybridoma and antibody are described in 78 Proc. Natl. Acad. Sci. 3199 (1981).

The procedure employed was substantially the same as the procedures of Examples I and II, except for the following. First, the step of dialyzing the chelate conjugated monoclonal antibody against ascorbate-EDTA was omitted. Second, 10 microliters of 0.1M ascorbate at pH 4 was added to the indium-111 solution prior its addition to the aqueous saline solution of the chelate conjugated monoclonal antibody.

The labeling efficiency exhibited a three-fold increase over the methods of Example I and II. The final product was labeled with approximately 2.1 microcuries per microgram.

Ten micrograms of the indium-III chelated conjugated monoclonal antibody collected from the purification column was diluted to 100 microliters with an aqueous solution of phosphate buffered saline. The diluted indium-III conjugated antibody was injected into the tail vein of a nude, athymic mouse in which a human breast tumor had been grown. The human breast tumor cells expressed an antigen for the antibody. Seventy-two hours after injection, a clear and well-defined gamma camera image demonstrated high localization of indium-111 in the tumor tissue. No similar localization of the indium-111 in the liver or spleen was observed.

Uses of the metal chelate conjugated monoclonal antibodies prepared according to this invention are described in more detail in copending application Ser. No. 386,109 entitled "Use of Metal Chelate Conjugated Monoclonal Antibodies" filed concurrently herewith.

Since modifications will be apparent to those skilled in the art, it is intended that this invention be limited only by the scope of the appended claims.

We claim:

1. A method of purifying metal chelate conjugated monoclonal antibodies comprising passing an aqueous solution containing metal chelate conjugated monoclonal antibodies through a chromatography column, said column having at least two different layers, an initial layer selected from a group consisting of an ion retardation resin, an anion exchange resin, a cation exchange resin and a chelating ion exchange resin, and a final layer comprising a sizing matrix.

2. The method of claim 1 wherein an initial layer of an ion retardation resin, a second layer of a cation exchange resin and a final sizing matrix layer are employed.

3. The method of claim 1 wherein said chelate conjugated monoclonal antibodies are prepared from diethylenetriaminepentaacetic acid.

4. A method of preparing metal chelate conjugated monoclonal antibodies comprising adding a metal salt to an aqueous solution of a chelate conjugated monoclonal antibodies and a buffer, said solution being maintained at a pH within the range of about 3.2 to about 9 throughout chelation without the addition of a strong acid or strong base.

5. The method of claim 4 wherein said buffer is citric acid.

6. The method of claim 4 wherein said chelation is carried out at a pH within the range of about 3.2 to about 3.5.

7. The method of claim 4 wherein said chelate conjugated monoclonal antibodies are prepared from diethylenetriaminepentaacetic acid.

8. A method for preparing metal chelate conjugated monoclonal antibodies comprising:
   (a) contacting a carboxycarbonic anhydride of diethylenetriaminepentaacetic acid with an aqueous solution of monoclonal antibodies at a pH maintained in the range from about 6 to about 7.2 to produce chelate conjugated monoclonal antibodies;
   (b) recovering said chelate conjugated monoclonal antibodies;
   (c) adding a metal salt to an aqueous solution of said recovered chelate conjugated monoclonal antibodies and a buffer to form metal chelate conjugated antibodies, said solution being maintained at a pH within the range of from about 3.2 to about 9 throughout chelation without the addition of a strong acid or strong base;
   (d) passing the aqueous solution containing said metal chelate conjugated monoclonal antibodies through a chromatography column, said column having one or more layers selected from the group consisting of an ion retardation resin, an anion exchange resin, a cation exchange resin and a chelating ion exchange resin, and a final layer comprising a sizing matrix; and
   (e) recovering from said column a solution of metal chelate conjugated antibodies having at least about 80% of said metal contained in said solution complexed by said chelate conjugated to said monoclonal antibodies.

9. The method of claim 8 wherein said carboxycarbonic anhydride of diethylenetriaminepentaacetic acid is the reaction product of an amine diethylenetriaminepentaacetic acid salt with an ester of a haloformic acid in an organic solvent at a temperature less than about −20° C.

10. The method of claim 9 wherein said ester of a haloformic acid is isobutylchloroformate.

11. The method of claim 8 wherein said metal salt is added to said aqueous chelate conjugated monoclonal antibody solution in an aqueous buffered solution containing ascorbic acid.

12. An aqueous solution of metal chelate conjugated monoclonal antibodies wherein the metal ion is in at least the +3 valence state, and in which at least about 94% of said metal is complexed by the chelate portion of said conjugate.

13. The solution of claim 12 wherein at least about 97% of said metal is complexed by the chelate portion of said conjugate.

14. The solution of claim 12 wherein said conjugated antibodies retain at least about 80% of their activity and specificity.

15. The solution of claim 12 wherein said conjugated antibodies retain at least about 95% of their activity and specificity.

16. The solution of claim 12 wherein said conjugated antibodies retain at least about 90% of their activity and specificity.

17. The solution of claim 12 wherein said conjugated antibodies retain substantially all of their activity and specificity.

18. The solution of claim 12 wherein said conjugated antibodies are formed employing diethylenetriaminepentaacetic acid.

19. The solution of claim 18 wherein said conjugated antibodies retain substantially all of their activity and specificity.

20. A method for preparing chelate conjugated monoclonal antibodies comprising:
   reacting an ester of a haloformic acid with an amine salt of diethylenetriaminepentaacetic acid in an organic solvent to produce carboxycarbonic anhydride of diethylenetriaminepentaacetic acid, said reaction carried out at a temperature sufficiently low to precipitate substantially all of the haloamine salt by-product;
   recovering said carboxycarbonic anhydride of diethylenetriaminepentaacetic acid by separating said organic solvent containing the anhydride in solution from said precipitated haloamine salt by-product;
   contacting said carboxycarbonic anhydride of diethylenetriaminepentaacetic acid with an aqueous solution containing monoclonal antibodies at a pH maintained in a range from about 6.0 to about 7.2 to produce chelate conjugated monoclonal antibodies; and
   recovering said chelate conjugated monoclonal antibodies having their biological activity and specificities substantially retained.

21. The method of claim 12 wherein the molar ratio of said carboxycarbonic anhydride of diethylenetriaminepentaacetic acid to said monoclonal antibodies in said contacting step is at least about 300:1.

22. The method of claim 20 wherein the concentration of said carboxycarbonic anhydride of diethylenetriaminepentaacetic acid recovered in the organic solvent is at least about 0.25M.

23. The method of claim 20 wherein said ester of a haloformic acid is isobutylchloroformate.

24. The method of claim 20 wherein said reaction temperature is in the range of from about −20° C. to about −70° C.

25. The solution of claim 13 wherein said conjugated antibodies retain at least 80% of their activity and specificity.

26. The solution of claim 13 wherein said conjugated antibodies retain at least 90% of their activity and specificity.

27. The solution of claim 13 wherein said conjugated antibodies retain at least 95% of their activity and specificity.

28. The solution of claim 13 wherein said conjugated antibodies retain substantially all of their activity and specificity.

29. The solution of claim 13 wherein said conjugated antibodies are formed employing diethylenetriaminepentaacetic acid.

* * * * *